United States Patent [19]

Al-Razzak et al.

[11] Patent Number: 5,334,589
[45] Date of Patent: Aug. 2, 1994

[54] QUINOLONE CARBOXYLIC ACID--METAL ION--ACID COMPLEXES

[75] Inventors: Laman A. Al-Razzak, Libertyville; Francisco J. Alvarez, Lindenhurst, both of Ill.

[73] Assignee: Abbott Laboratories, Abbott Park, Ill.

[21] Appl. No.: 867,200

[22] Filed: Jun. 25, 1992

Related U.S. Application Data

[63] Continuation-in-part of Ser. No. 458,927, Dec. 29, 1989, abandoned.

[51] Int. Cl.⁵ ............... A61K 31/47; C07D 215/56
[52] U.S. Cl. ..................... 514/185; 514/191; 514/228.2; 514/235.2; 514/254; 514/255; 514/314; 544/14; 544/225; 544/233; 546/2; 546/61; 546/64
[58] Field of Search ............. 514/185, 191, 228.2, 514/235.2, 254, 255, 314; 544/14, 225, 233; 546/2, 61, 64

[56] References Cited

U.S. PATENT DOCUMENTS

| | | |
|---|---|---|
| 4,705,789 | 11/1987 | Grohe et al. . |
| 4,730,000 | 3/1988 | Chu .................. 514/254 |
| 4,808,583 | 2/1989 | Grohe et al. . |

FOREIGN PATENT DOCUMENTS

| | | |
|---|---|---|
| 287926A2 | 10/1988 | European Pat. Off. . |
| 470667A1 | 2/1992 | European Pat. Off. . |
| 2264724 | 10/1990 | Japan . |

OTHER PUBLICATIONS

Nakano et al., Chem. Pharm. Bull. 26(5):1505–1510 (1978).

*Primary Examiner*—Nathan M. Nutter
*Attorney, Agent, or Firm*—Andreas M. Danckers

[57] ABSTRACT

Compositions of a quinolone carboxylic acids useful for oral or parenteral administration to a human or veterinary patient are disclosed which comprise quinolone carboxylic acid—metal ion—acid complexes in combination with a physiologically acceptable carrier and having a pH of about 4 to about 10, as well as a method for their production and use in treatment. Such compositions are found to cause unexpectedly low levels of vein irritation upon intravenous administration.

9 Claims, No Drawings

QUINOLONE CARBOXYLIC ACID--METAL ION--ACID COMPLEXES

This application is a continuation-in-part of copending U.S. application Ser. No. 07/458,927, filed Dec. 29, 1989.

TECHNICAL FIELD

The present invention is directed to compositions containing and methods of preparing quinolone carboxylic acid—metal ion—acid complexes and their use in treating bacterial infections. In particular, the invention is directed to such compositions which are suitable for intravenous administration with reduced venous irritation.

BACKGROUND OF THE INVENTION

Quinolone caroxylic acids are known to be effective antibacterial agents. Some of these compounds, however, have low solubility at neutral pH values, a characteristic which can adversely affect their suitability for parenteral administration to patients. Moreover, a common side-effect of intravenous administration is discomfort due to venous irritation. Hemolysis is a further undesirable side-effect which may in some instances be observed upon intravenous administration of quinolone carboxylic acids.

One especially effective quinolone carboxylic acid antibacterial compound is temafloxacin, a quinolone 3-carboxylic acid represented by the formula:

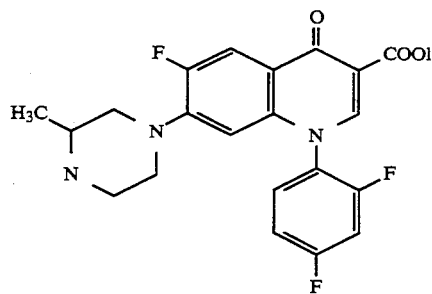

and having the chemical name 1-(2,4-difluorophenyl)-6-fluoro-1,4-dihydro-7-(3-methyl-l-piperazinyl)-4-oxo-3-quinoline carboxylic acid. Temafloxacin is disclosed in U.S. Pat. No. 4,730,000, issued to Chu.

Temafloxacin and its derivatives and salts have antibacterial activity, and are known to be useful for combating bacterial infections in warm-blooded animals. The solubility of temafloxacin base in water, however, is less than 0.5 mg/ml. Acidic or basic salts can be prepared at extreme pH values, as for example less than pH 4 for acid salts or greater than pH 10 for basic salts. Unfortunately, such solutions may be unsuitable for parenteral formulations due to their non-physiological pH, which upon injection is believed to contribute to the above-mentioned venous irritation. Moreover, these solutions are relatively physically unstable at high concentrations, as for example those greater than 10 mg/ml.

The preparation of certain parenterally administrable compositions of quinolone carboxylic acids has been reported by Preiss et al. in European Patent Application No. 287 926 and by Grohe et al. in U.S. Pat. Nos. 4,808,583 and 4,705,789. The application of Preiss et al. discloses the preparation of highly purified quinolone carboxylic acids said to be suitable for administration in parenteral solution. The highly purified quinolone carboxylic acid is prepared by dissolving the quinolone, or a salt thereof, with an acid, preferably in the presence of activated charcoal. The mixture is maintained for 0.15 to 150 hours, after which it is filtered and the quinolone carboxylic acid precipitated by addition of a basic reagent. The precipitated quinolone carboxylic acid is then dissolved for parenteral use. This method reportedly produces stable pharmacological solutions of quinolone carboxylic acids such as ciprofloxacin.

The above U.S. patents of Grohe et al. disclose lactic acid salts of quinolone carboxylic acids, as well as acid addition salts, that are said to be stable in solution at pH values of between 2.5 and 7 but more reliably at pH values of between 3.5 and 4.5. Quinolone carboxylic acids, or salts thereof, are dissolved in lactic acid, followed by the adjustment of concentration with water, or titration of pH with sodium hydroxide or acids such as methanesulfonic acid or propionic acid.

However, higher-concentration solutions of quinolone carboxylic acids which are chemically and physically stable near physiological pH, and which are suitable for parenteral administration to human or veterinary patients, have not been reported in the literature. Also, many formulations of quinolone carboxylic acids have been observed to produce hemolysis upon infusion. There consequently remains a need for stable compositions of quinolone carboxylic acids which do not produce the venous irritation and/or hemolysis frequently observed when known compositions are administered intravenously.

SUMMARY OF THE INVENTION

The present invention is directed to compositions of a quinolone carboxylic acid, such as temafloxacin, that are useful for oral or parenteral administration to a human or veterinary patient. The compositions of the present invention comprise quinolone carboxylic acid—metal ion—acid complexes, such as a complex of temafloxacin with a di- or trivalent metal cation and an acid, dissolved in a physiologically acceptable carrier which is adjusted, when necessary, to a pH of about 4 to about 10 and a desired concentration. More preferable, the pH is adjusted to a pH of about 6 to about 8. These compositions are especially useful for intravenous administration in that they exhibit reduced venous irritation upon injection and have been found to diminish the hemolysis which occurs upon infusion of the quinolone carboxylic acid alone.

The present invention also encompasses a method of preparing a stable composition of a quinolone carboxylic acid—metal ion—acid complex at a neutral pH. In one possible preparation according to the invention, a quinolone carboxylic acid is suspended in a solution of a di- or trivalent metal salt. The suspension is then either acidified or made alkaline, followed by adjustment of the solution to a pH of about 4 to about 10. The solution containing the dissolved complex is then filtered and stored for use.

A method for treating bacterial infections is also encompassed within the present invention. In this method, a parenteral or oral composition of a quinolone carboxylic acid—metal ion—acid complex is administered to a human or veterinary patient in need of such treatment. The complex is administered, preferably either intravenously or intramuscularly, at a therapeutically effective dosage sufficient to produce an antibacterial effect.

DETAILED DESCRIPTION OF THE INVENTION

The present invention is directed to compositions and methods for treating bacterial infections.

In one aspect of the present invention are disclosed compositions comprising a salt complex of a quinolone carboxylic acid in stable solution with a pharmaceutically acceptable carrier and having a pH of about 4 to about 10. These compositions are found to be physically stable at high concentration, and to cause an unexpectedly reduced degree of venous irritation upon intravenous injection, when compared to previously known compositions.

The term "quinolone carboxylic acid" as used herein refers to not only the commonly known quinolone antibiotics and their derivatives but also to salts thereof. Examples of quinolone carboxylic acids which may benefit from formulation in a composition of the invention include temafloxacin, ciprofloxacin, norfloxacin, sarafloxacin and difloxacin as well as their hydrochloride and similar salts. Other quinolone carboxylic acids may also possess low solubility and/or cause venous irritation upon injection, and may be more readily administrable if prepared as one of the complexes of the present invention.

The term "complex" as used herein refers to the association of a quinolone carboxylic acid with a metal ion and an organic or inorganic acid. In addition, such complexes can have associated with them a basic counterion. While not intending to be limited by theory, it is believed that these complexes prinicipally involve the association of the 3-carboxylic acid and 4-oxo functionalities, respectively, with the polyvalent metal ion. Consequently, it is anticipated that compounds other than the above quinolones may be formulated according to the present invention as well.

Metal ions suitable for use in the present invention include those which are capable of forming the above complexes and which are physiologically tolerated at the concentrations necessary to produce an effective dose of the quinolone carboxylic acid being administered. Examples include divalent metal ions such as magnesium, calcium, manganese, zinc, cadmium, ferrous ($Fe^{2+}$) and the like, as well as trivalent metal ions such as aluminum, cerium ($Ce3+$), ferric ($Fe^{3+}$) and the like. A preferred metal ion for use in the compositions of the invention is magnesium.

Acids which are suitable in forming the complexes of the present invention include organic acids such as lactic acid, acetic acid, nicotinic acid, toluenesulfonic acid, methanesulfonic acid, lactobionic acid, mandelic acid, isethionic acid, glucuronic acid, cysteic acid and the like. A preferred acid for use in the invention is glucuronic acid.

The term "physiologically acceptable carrier" as used herein refers to any diluent or other formulating auxiliary that is compatible with the other ingredients of the composition and is not deleterious to the patient. The physiologically acceptable carrier can take a variety of forms, depending upon the formulation desired for administration and the intended route of administration. Illustrative carriers for parenteral administration include water, physiological saline, Ringer's solution and the like, but may also include other aqueous or nonaqueous solvents or vehicles such as alcohols, polyols, vegetable oils, injectable organic esters such as ethyl oleate, and mixtures thereof. Prevention of the action of microorganisms may be ensured by the inclusion of various antibacterial and antifungal agents, as for example paraben, chlorobutanol, phenol, sorbic acid, and the like. It may also be desirable to include isotonic agents such as sugars, sodium chloride and the like.

In another aspect of the present invention is disclosed a method for preparing the compositions of the invention, comprising first suspending a quinolone carboxylic acid in a solution of a metal ion salt and then producing therefrom a solution of a quinolone carboxylic acid—metal ion—acid complex at a pH of about 4 to about 10. The formation of a solution of the complex may be accomplished in several ways. For example, where the suspended quinolone carboxylic acid is in a base form such as temafloxacin base, the suspension may be treated with an excess of acid such as HCl or methanesulfonic acid before titration with a base back towards a dissolved complex of more neutral pH. The pH attained before titration may be as low as pH 1, although less acidic conditions will usually be sufficient.

Alternatively, a quinolone carboxylic acid may first be suspended and treated with an excess of base such as NaOH, followed by titration with an acid back towards a dissolved complex having the desired pH range. The pH thus attained before titration may be as low as pH 12; again, less alkaline conditions will usually suffice to bring about formation of the dissolved complex.

In another alternative method found to be suitable when the suspended quinolone carboxylic acid is an acid salt such as temafloxacin hydrochloride, the suspension may be directly titrated with a base towards a dissolved complex of more neutral pH.

In each instance, particulate matter may be then be removed as by filtration. The solution may also be sterilized prior to use, as for example by filtration through a bacteria-retaining filter or by the incorporation of sterilizing agents.

Examples of acids useful in the method of the present invention are those which are physiologically tolerated, including organic acids such as those already named as well as inorganic acids such as hydrochloric acid, phosphoric acid, sulfuric acid, nitric acid and the like. Bases which may be employed are those which likewise may be administered without undue risk to the patient, and include lysine, arginine, ethylenediamine, choline, ethanolamine, dibenzylethylenediamine and the like.

Solubilities of complexes of quinolone carboxylic acids prepared according to the above method are substantially improved over those previously obtained at or near neutral pH. For example, the solubility of a temafloxacin complex of the present invention is increased to about 300 mg/ml, at about pH 4 to about pH 10, as compared to a solubility of temafloxacin of less than about 0.5 mg/ml at similar pH values. The compositions of the present invention are therefore capable of solution at concentrations which are more than 600-fold greater, at pH values of about 4 to about 10, than those of quinolone carboxylic acids that are not associated in complexes such as those of the invention.

In yet another aspect of the present invention is disclosed a method for treating a bacterial infection in a human or veterinary patient, comprising administering to said patient, for a time period sufficient to produce an antibacterial effect, a therapeutically effective amount of a composition of the invention. The term "therapeutically effective" as used herein refers to a sufficient amount of the compound to treat bacterial infection at a reasonable benefit/risk ratio applicable to any medical treatment. It is intended, however, that the total daily usage of the compositions of the present invention will be decided by the attending physician within the scope of sound medical judgement. Actual dosage levels of active ingredients in the pharmaceutical compositions of this invention may be varied so as to obtain an amount of the active compound(s) that is effective to achieve the desired therapeutic response for a particular patient, compositions, and mode of administration. The selected dosage level will depend upon a variety of factors, including the activity of the particular compound, the route of administration, the severity of the condition being treated, and the condition and prior medical history of the patient being treated.

Particular examples of the complexes of the present invention include the following:

1-(2,4-difluorophenyl)-6-fluoro-1,4-dihydro-7-(3-methyl-1-piperazinyl)-4-oxo-3-quinoline carboxylic acid—Mg—HCl (temafloxacin—Mg—HCl);

1-(2,4-difluorophenyl)-6-fluoro-1,4-dihydro-7-(3-methyl-1-piperazinyl)-4-oxo-3-quinoline carboxylic acid—Mg—methanesulfonate (temafloxacin—Mg—methanesulfonate);

1-(2,4-difluorophenyl)-6-fluoro-1,4-dihydro-7-(3-methyl -1-piperazinyl)-4-oxo -3-quinoline carboxylic acid—Mg—isethionate (temafloxacin—Mg—isethionate);

1-(2,4-difluorophenyl)-6-fluoro-1,4-dihydro-7-(3-methyl-1-piperazinyl)-4-oxo-3-quinoline carboxylic acid—Ca—HCl (temafloxacin—Ca—HCl);

1-(2,4-difluorophenyl)-6-fluoro-1,4-dihydro-7-(3-methyl-1-piperazinyl)-4-oxo-3-quinoline carboxylic acid—Al-methanesulfonate (temafloxacin—Al—methanesulfonate);

1-(2,4-difluorophenyl)-6-fluoro-1,4-dihydro-7-(3-methyl-1-piperazinyl)-4-oxo-3-quinoline carboxylic acid—Mg—glucuronate (temafloxacin—Mg—glucuronate);

1-(2,4-difluorophenyl)-6-fluoro-1,4-dihydro-7-(3-methyl-1-piperazinyl)-4-oxo-3-quinoline carboxylic acid—Mg—lactate (temafloxacin—Mg—lactate);

1-(2,4-difluorophenyl)-6- fluoro-1,4-dihydro-7-(3-methyl-1-piperazinyl)-4-oxo-3-quinoline carboxylic acid—Mg—mandelate (temafloxacin—Mg—mandelic acid);

1-(2,4-difluorophenyl)-6-fluoro-1,4-dihydro-7-(3-methyl-1-piperazinyl)-4-oxo-3-quinoline carboxylic acid—Mg—cysteate (temafloxacin—Mg—cysteic acid); and 1-(2,4-difluorophenyl)-6-fluoro-1,4-dihydro-7-(3-methyl-1-piperazinyl)-4-oxo-3-quinoline carboxylic acid HCl—Mg—choline (temafloxacin HCl—Mg—choline).

Of these, a preferred complex is 1-(2,4-difluorophenyl)-6-fluoro-1,4-dihydro-7-(3-methyl-1-piperazinyl)-4-oxo-3-quinoline carboxylic acid—Mg—glucuronate (temafloxacin—Mg—glucuronate), and especially temafloxacin—Mg—glucuronate—NaOH and temafloxacin—Mg—glucuronate—lysine, in which the preferred complexes are titrated with NaOH and lysine, respectively.

The present invention is further described in the following Examples, which are intended as illustrative of the invention claimed herein and not as a limitation upon the scope thereof.

EXAMPLE 1

1-(2,4-difluorophenyl)-6-fluoro-1,4-dihydro-7-(3-methyl-1-piperazinyl-4-oxo-3-quinoline carboxylic acid—Mg—HCl A solution of temafloxacin—Mg—HCl suitable for intravenous administration was prepared by a procedure in which magnesium chloride hexahydrate (5.6 gm, 2.5 equivalents) was dissolved in 900 ml of water for injection (WFI). Temafloxacin hydrochloride (5.0 gm, 11 mmoles) was suspended in this solution.

L-Arginine (1.93 gm, 1 equivalent) was next added to neutralize the solution and to dissolve the temafloxacin. The pH was adjusted to pH 7 with an L-arginine solution, and sodium chloride (6.2 gm) was added to adjust for isotonicity. The resultant solution was adjusted to 1 liter with WFI and filter-sterilized through a 0.2 micron filter to produce a 4.6 mg/ml solution (in terms of equivalent weight of temafloxacin base) of the temafloxacin—Mg—HCl complex at pH 7.

EXAMPLE 2

1-12,4-difluorophenyl)-6-fluoro-1,4-dihydro-7-(3-methyl-1-piperazinyl)-4-oxo-3-quinoline carboxylic acid—Mg—methanesulfonate A stable solution of temafloxacin—Mg—methanesulfonate complex was prepared by a procedure in which temafloxacin base (2.0 gm, 4.8 mmoles) was suspended in water (20 ml) and a 1 M MgCl$_2$ solution (12 ml). The solution was stirred for 30 minutes, and methanesulfonic acid (neat, 400 μl) was added until the pH of the solution was about pH 1.5. An arginine solution was added dropwise until the solution cleared and the pH was between about pH 6.6 and about pH 6.9.

Water (180 ml) was added and the solution was filtered through a 0.2 micron filter and adjusted to 200 ml with sterile water to produce a 10 mg/ml solution of the complex.

EXAMPLE 3

1-(2,4-difluorophenyl)-6-fluoro-1,4-dihydro-7-(3-methyl-1-piperazinyl)-4-oxo-3-quinoline carboxylic acid—Mg—isethionate A stable solution of a temafloxacin—Mg—isethionate complex was prepared by the procedure described in Example 2 by substituting 5 ml of a 1 M isethionic acid solution for methanesulfonic acid.

EXAMPLE 4

1-(2,4-difluorophenyl}-6-fluoro-1,4-dihydro-7-(3-methyl-1-piperazinyl)-4-oxo-3-quinoline carboxylic acid—Ca—HCl A stable solution of a temafloxacin—Ca—HCl complex was prepared by a procedure in which temafloxacin-HCl (98.1 gm, 0.216 moles) was suspended in a calcium chloride solution (2-to-3 M, 216 ml) and adjusted to neutral pH with 1N NaOH (216 ml). Water (315 ml) was added and the solution stirred until all of the temafloxacin dissolved. The pH was adjusted to pH 6.2 with 1N NaOH and the volume was adjusted to 900 ml with water. The solution was filtered through a 0.2 micron filter to produce a 100 mg/ml solution (by weight of temafloxacin base) of the complex.

EXAMPLE 5

1(2,4,difluorophenyl)-6-fluoro-1,4-dihydro-7-(3-methyl-1-piperazinyl)-4oxo-3-quinoline carboxylic acid—Ca—HCl Alternatively, a stable solution of a temafloxacin—Ca—HCl complex was prepared by a procedure in which temafloxacin base .(220 mg, 0.53 mmoles) was suspended in 0.1 M CaCl₂ (10 ml, 2 molar equivalents of Ca²⁺ ion). Sodium hydroxide (1 N, 550 μl) was added to the solution and stirred. The resulting suspension (about pH 11) was adjusted to neutral pH and clarified with 1 N HCl (200–400 μl) to a final pH of between pH 7 and pH 8. The solution was filtered through a 0.2 micron filter to produce a 20-to-21 mg/ml solution of the complex.

EXAMPLE 6

1-12,4=difluorophenyl)-6-fluoro-1,4-dihydro-7-(3-methyl-1-piperazinyl)-4-oxo-3-quinoline carboxylic acid-Al—methanesulfonate A stable solution of temafloxacin—Al—methanesulfonate complex was prepared by a procedure in which temafloxacin-HCl (500 mg, 0.92 moles) was suspended in a solution of aluminum methanesulfonate (0.27 M, 0.40 Moles) together with water (2.0 ml). The pH was adjusted to 6.5 with 1 N NaOH. The solution was filtered to produce an approximately 100 mg/ml solution (by weight of temafloxacin base) of the complex.

EXAMPLE 7

1-(2,4-difluorophenyl)-6-fluoro-1,4-dihydro-7-(3-methyl-1-piperazinyl)-4-oxo-3-quinoline carboxylic acid—Mg—glucuronate A stable solution of temafloxacin—Mg—glucuronate was prepared by a procedure in which temafloxacin base (800 mg, 1.92 Moles) was suspended in a solution of magnesium chloride hexahydrate (584.2 mg, 2.88 mmoles) in 100 ml 5% dextrose in water. D-Glucuronic acid (409.9 mg, 2.11 Moles) was added and the resulting mixture stirred for 10 minutes. The resulting solution (pH approximately 3.59) was then titrated dropwise with 1 N NaOH until clear (pH approximately 6.7) and filtered through a 0.45 micron filter. The volume was increased to 200 ml with 5% dextrose in water and the solution (pH approximately 6.9) passed through a 0.2 micron filter.

EXAMPLE 8

1-(2,4-difluorophenyl)-6-fluoro-1,4-dihydro-7-(3-methyl-1-piperazinyl)-4-oxo-3-quinoline carboxylic acid-Mg—glucuronate Alternatively, a stable solution of temafloxacin—Mg—glucuronate was prepared by a procedure in which temafloxacin base (435.2 mg) was mixed with 50 ml normal saline to which had been added 0.96 ml of 1 N NaOH solution. After 5 minutes of stirring, glucuronic acid (223.3 mg) was added, and the mixture stirred another 5 minutes. The resulting suspension was titrated until clear with 1 N NaOH (approximately 1.0 ml) and filtered through a 0.45 micron filter. The volume of the solution (pH approximately 6.7) was then increased to 100 ml with WFI and passed through a 0.2 micron filter.

EXAMPLE 9

1-(2,4-difluorophenyl)-6-fluoro-1,4-dihydro-7-(3-methyl-1-piperazinyl)-4-oxo-3-quinoline carboxylic acid—Mg—glucuronate—lysine A stable solution of temafloxacin—Mg—glucuronate—lysine was prepared by the procedure of Example 7, except that 1 N lysine (1 ml) was used in place of NaOH.

EXAMPLE 10

1-(2,4-difluorophenyl)-6-fluoro-1,4-dihydro-7-(3-methyl-1-piperazinyl)-4-oxo-3-quinoline carboxylic acid—Mg—glucuronate—choline A stable solution of temafloxacin—Mg—glucuronate—choline was prepared by the procedure of Example 7, except that 1 N choline base (1 ml) was used in place of NaOH.

EXAMPLE 11

1-(2,4-difluorophenyl)-6-fluoro-1,4-dihydro-7-(3-methyl-1-piperazinyl)-4-oxo-3-quinoline carboxylic acid—Mg—lactate A stable solution of temafloxacin—Mg—lactate was prepared by the procedure of Example 7, except that 225 mg lactic acid USP (2.5 moles) was used in place of glucuronic acid.

EXAMPLE 12

1-(2,4-difluorophenyl)-6-fluoro-1,4-dihydro-7-(3methyl-1-piperazinyl)-4-oxo-3-quinoline carboxylic acid—Mg—mandelate A stable solution of temafloxacin—Mg—mandelate was prepared by the procedure of Example 7, except that 350.5 mg mandelic acid (2.3 moles) was used in place of glucuronic acid.

EXAMPLE 13

1-(2,4-difluorophenyl]-6-fluoro-1,4-dihydro-7-(3methyl-1-piperazinyl)-4-oxo-3-quinoline carboxylic A stable solution of temafloxacin—Mg—cysteate can be prepared by the procedure of Example 7, except that 390 mg cysteic acid is used in place of glucuronic acid.

EXAMPLE 14

1-(2,4-difluorophenyl)-6-fluoro-1,4-dihydro-7-(3-methyl-1-piperazinyl)-4-oxo-3-quinoline carboxylic acid HCl—Mg—choline A stable solution of temafloxacin HCl—Mg—choline was prepared by a procedure in which temafloxacin HCl (454 mg, 1 mmole) and magnesium chloride hexahydrate (304 mg, 1.5 mmoles) were suspended in 75 ml of normal saline and stirred for 10 minutes (pH approximately 3.8). Choline base (neat, approximately 100 μl) was added dropwise until a clear solution was formed at a pH of approximately 6.7. The solution was then filtered through a 0.45 micron filter and the volume increase to 100 ml with normal saline. This solution was then passed through a 0.2 micron filter (pH approximately 6.97, osmolarity 338).

EXAMPLE 15

Vein Irritation in Rats

Compositions of the present invention were tested for vein irritation upon intravenous administration using a rat tail vein model, in which discoloration of the tail is observed following daily infusion of a test preparation. Three studies were conducted: In Study I, four rats per group were given test compositions for three consecutive days at a concentration of 4 mg/ml (this and other concentrations expressed in terms of equivalent weight of temafloxacin base); in Study II, three rats per group were given test compositions for five consecutive days at 6 mg/ml; and in Study III, two groups of three rats each were given test compositions for five consecutive days at 4 mg/ml and 8 mg/ml, respectively. All rats were dosed at 100 mg/kg/day, with an infusion rate of 0.3 ml/minute.

Each rat was observed twice after each infusion: Once after 1-to-2 hours following injection, and again after 24 hours. Discoloration was ranked as follows:

5 = Normal tail appearance
4 = Single red/pink spot of discoloration
3 = Multiple red/pink spots of discoloration
2 = Single purple spot of discoloration
1 = Multiple purple spots of discoloration
0 = Approx. one-fourth of distal tail discolored purple Aggregate rankings were totaled for each group over the course of each study. Totals and normalized rankings (computed as the group total divided by the number of animals divided by the number of measurements), shown in Table 1 below, demonstrate the reduction of vein irritation obtained by formulating temafloxacin as one of the complexes of the present invention.

TABLE 1

| Composition Tested* | Study | Total Rank | Normalized Rank |
| --- | --- | --- | --- |
| Example 7 | I | 94 | 3.92** |
| Example 7 (D5W) | II | 95 | 3.17 |
| Example 7 | II | 125 | 4.17** |
| Example 7 (4 mg/ml) | III | 95 | 3.17 |
| Example 7 (8 mg/ml) | III | 91 | 3.03 |
| Example 9 | II | 121 | 4.03 |
| Example 10 | II | 118 | 3.93 |
| Example 11 | I | 79 | 3.29 |
| Example 12 | II | 85 | 2.83 |
| Example 14 | I | 88 | 3.67 |
| Control A*** | I | 55 | 2.29 |
| Control B*** | II | 97 | 3.23 |
| Control C*** | II | 109 | 3.63 |

Control A = Lysine salt of temafloxacin.
Control B = Sodium salt of temafloxacin.
Control C = Normal saline only.
Saline = Final composition prepared using normal saline.
* = All compositions prepared using normal saline except where indicated (D5W = 5% dextrose in water).
** = No purple discoloration noted on any animal.
*** = A fourth control group, in which temafloxacin HCl was administered at 4 mg/ml in normal saline, was discontinued after the first day due to extreme irritation and necrosis near the site of injection.

A fourth study was conducted to further compare the most favorable of the above compositions. In Study IV, two groups of three rats each were given test compositions (in normal saline) for five consecutive days at 6 mg/ml. All rats were dosed at 100 mg/kg/day, with an infusion rate of 0.3 ml/minute. Scoring was as before, and was again normalized for comparison. The results, shown below in Table 2, demonstrate the low level of vein irritation occurring with the preferred compositions temafloxacin—Mg—glucuronate—lysine (Example 9) and temafloxacin—Mg—glucuronate—NaOH (Example 7).

TABLE 2

| Composition Tested | Day | Total Rank | Normalized Rank |
| --- | --- | --- | --- |
| Example 7 | 3 | 70 | 3.89 |
|  | 4 | 89 | 3.71 |
|  | 5 | 112 | 3.71 |
| Example 9 | 3 | 81 | 4.50 |
|  | 4 | 106 | 4.42 |
|  | 5 | 132 | 4.40 |

The above results demonstrate the reduction in vein irritation obtainable when the compositions of the present invention are used for parenteral administration of a quinolone carboxylic acid.

The foregoing description and Examples are intended as illustrative and are not to be taken as limiting. Still other variations of the invention are possible which are within the spirit and scope of the claims which follow, and which will be readily apparent to those skilled in the art.

We claim:

1. A pharmaceutical composition comprising a quinolone carboxylic acid—metal ion—acid complex dissolved in a physiologically acceptable carrier and having a pH of about 4 to about 10.

2. A composition according to claim 1 wherein said metal ion is selected from the group consisting of magnesium and calcium.

3. A composition according to claim 1 wherein said complex is selected from the group consisting of:

1-(2,4-difluorophenyl)-6-fluoro-1,4-dihydro-7-(3-methyl-1-piperazinyl)-4-oxo-3-quinoline carboxylic acid—Mg—HCl;

1-(2,4-difluorophenyl)-6-fluoro-1,4-dihydro-7-(3-methyl-1-piperazinyl)-4-oxo-3-quinoline carboxylic acid—Mg—methanesulfonate;

1-(2,4-difluorophenyl)-6-fluoro-1,4-dihydro-7-(3-methyl-1-piperazinyl)-4-oxo-3-quinoline carboxylic acid—Mg—isethionate;

1-(2,4-difluorophenyl)-6-fluoro-1,4-dihydro-7-(3-methyl-1-piperazinyl)-4-oxo-3-quinoline carboxylic acid—Ca—HCl;

1-(2,4-difluorophenyl)-6-fluoro-1,4-dihydro-7-(3-methyl-1-piperazinyl)-4-oxo-3-quinoline carboxylic acid—Al—methanesulfonate;

1-(2,4-difluorophenyl)-6-fluoro-1,4-dihydro-7-(3-methyl-1-piperazinyl)-4-oxo-3-quinoline carboxylic acid—Mg—glucuronate;

1-(2,4-difluorophenyl)-6-fluoro-1,4-dihydro-7-(3-methyl-1-piperazinyl)-4-oxo-3-quinoline carboxylic acid—Mg—lactate;

1-(2,4-difluorophenyl)-6-fluoro-1,4-dihydro-7-(3-methyl-1-piperazinyl)-4-oxo-3-quinoline carboxylic acid—Mg—mandelate;

1-(2,4-difluorophenyl)-6-fluoro-1,4-dihydro-7-(3-methyl-1-piperazinyl)-4-oxo-3-quinoline carboxylic acid—Mg—cysteate; and 1-(2,4-difluorophenyl)-6-fluoro-1,4-dihydro-7-(3-methyl-1-piperazinyl)-4-oxo-3-quinoline carboxylic acid HCl—Mg—choline.

4. A composition according to claim 1 wherein said quinolone carboxylic acid is 1-(2,4-difluorophenyl)-6-fluoro-1,4-dihydro-7-(3-methyl-l-piperazinyl)-4-oxo-3-quinoline carboxylic acid, said metal ion is magnesium and said acid is glucuronic acid.

5. A method of preparing a composition according to claim 1 comprising:

(a) suspending an acid salt of a quinolone carboxylic acid in a solution of a metal ion salt to produce a suspension of a quinolone carboxylic acid—metal ion—acid complex; and (b) adjusting the pH of said suspension to a pH of about 4 to about 10 with an alkaline solution to dissolve said complex.

6. A method of preparing a composition according claim 1 comprising:

(a) suspending a quinolone carboxylic acid in a solution of a metal ion salt; and (b) producing a solution of a quinolone carboxylic acid—metal ion—acid complex at a pH of about 4 to about 10.

7. A method according to claim 6 wherein said complex solution is produced by the steps of:

(a) adding an acid to said suspension to lower the pH of said suspension; and (b) adding a sufficient amount of a base to form a solution of quinolone carboxylic acid—metal ion—acid complex having a pH of about 4 to about 10.

8. A method according to claim 6 wherein said complex solution is produced by the steps of:

(a) adding a base to said suspension to raise the pH of said suspension; and (b) adding a sufficient amount of an acid to form a solution of quinolone carboxylic acid—metal ion-acid complex having a pH of about 4 to about 10.

9. A method according to claim 6 wherein said quinolone carboxylic acid is 1-(2,4-difluorophenyl)-6-fluoro-1,4-dihydro-7-(3-methyl-1-piperazinyl)-4-oxo-3-quinoline carboxylic acid and said metal ion is magnesium.

* * * * *